United States Patent
Mertens et al.

(10) Patent No.: US 12,076,670 B2
(45) Date of Patent: Sep. 3, 2024

(54) METHOD FOR OPERATING A DISTILLATION COLUMN

(71) Applicants: Covestro Deutschland AG, Leverkusen (DE); Covestro Intellectual Property GmbH & Co. KG, Leverkusen (DE)

(72) Inventors: Klaus Mertens, Moers (DE); Sabine Pegel, Düsseldorf (DE)

(73) Assignees: Covestro Deutschland AG, Leverkusen (DE); Covestro Intellectual Property GmbH & Co. KG, Leverkusen (DE)

( * ) Notice: Subject to any disclaimer, the term of this patent is extended or adjusted under 35 U.S.C. 154(b) by 154 days.

(21) Appl. No.: 17/781,413

(22) PCT Filed: Dec. 9, 2020

(86) PCT No.: PCT/EP2020/085198
§ 371 (c)(1),
(2) Date: Jun. 1, 2022

(87) PCT Pub. No.: WO2021/116146
PCT Pub. Date: Jun. 17, 2021

(65) Prior Publication Data
US 2023/0008804 A1  Jan. 12, 2023

(30) Foreign Application Priority Data

Dec. 12, 2019 (EP) ................................ 19215603
Dec. 1, 2020 (EP) ................................ 20210976

(51) Int. Cl.
*B01D 3/42* (2006.01)
*C07C 201/16* (2006.01)

(52) U.S. Cl.
CPC ............ *B01D 3/425* (2013.01); *C07C 201/16* (2013.01)

(58) Field of Classification Search
CPC ...... B01D 3/425; B01D 3/4211; C07C 201/16
See application file for complete search history.

(56) References Cited

U.S. PATENT DOCUMENTS 3,428,528 A * 2/1969 Keeler ................. B01D 3/4255
700/270
3,463,725 A * 8/1969 Macfarlane .......... B01D 3/4238
203/99

(Continued)

FOREIGN PATENT DOCUMENTS

CN  105017004 A  11/2015

OTHER PUBLICATIONS

International Search Report, PCT/EP2020/085198, date of mailing: Feb. 22, 2021, Authorized officer: J. Van Ganswijk.

*Primary Examiner* — Jonathan Miller
(74) *Attorney, Agent, or Firm* — Donald R. Palladino

(57) ABSTRACT

The present invention relates to a method for continuously operating a distillation column, which is designed to separate a mixture S, which contains essentially a substance A and a substance B, which boils significantly higher than substance A. In the method according to the invention, the reflux ratio is changed according to the feed flow and, at the same time, the energy input by means of the heat-transfer medium is changed proactively (so-called feed-forward control) by accounting for the feed flow by means of feed-forward control. At the same time, the bottom temperature is observed and the control structure is changed if the bottom temperature falls too far when the heat-transfer medium is reduced by means of the feed flow.

5 Claims, 3 Drawing Sheets

(56) References Cited

U.S. PATENT DOCUMENTS

| | | | | |
|---|---|---|---|---|
| 3,826,719 | A * | 7/1974 | Boyd et al. | B01D 3/4227 700/270 |
| 3,855,074 | A * | 12/1974 | Mosler | B01D 3/4255 700/270 |
| 3,905,873 | A * | 9/1975 | Wright | B01D 3/425 203/1 |
| 4,024,027 | A * | 5/1977 | Boyd | B01D 3/4238 203/99 |
| 4,096,574 | A * | 6/1978 | Christie | B01D 3/425 700/270 |
| 4,166,770 | A * | 9/1979 | Anderson | G06G 7/58 700/270 |
| 4,230,534 | A * | 10/1980 | Stewart | B01D 3/425 700/270 |
| 4,252,614 | A * | 2/1981 | Stewart | B01D 3/4255 700/270 |
| 4,367,121 | A * | 1/1983 | Furr | B01D 3/4222 700/270 |
| 5,260,865 | A * | 11/1993 | Beauford | B01D 3/425 700/270 |
| 6,088,630 | A * | 7/2000 | Cawlfield | G05B 17/02 700/270 |
| 8,419,903 | B2 | 4/2013 | Bahr | |
| 11,225,444 | B2 * | 1/2022 | Al-Dughaiter | B01D 3/4205 |
| 11,235,260 | B2 * | 2/2022 | Schweigert | C07C 17/383 |
| 11,702,381 | B1 * | 7/2023 | Pennemann | B01D 3/4205 203/2 |
| 2013/0018210 | A1 * | 1/2013 | Guenkel | C07C 201/16 568/940 |

* cited by examiner

METHOD FOR OPERATING A DISTILLATION COLUMN

CROSS-REFERENCE TO RELATED APPLICATION

This application is a national stage application under 35 U.S.C. § 371 of PCT/EP2020/085198, filed Dec. 9, 2020, which claims the benefit of European Application Nos. 19215603.2, filed Dec. 12, 2019, and 20210976.5, filed Dec. 1, 2020, each of which is incorporated herein by reference.

FIELD

The present invention relates to a method of continuously operating a distillation column set up for separation of a substance mixture S comprising essentially a substance A and a substance B which is significantly higher-boiling than substance A. In the method of the invention, the reflux ratio is varied as a function of the feed stream and, at the same time, the energy input by the heat carrier medium is altered proactively (what is called feedforward control) by accounting for the feed stream by means of feedforward control. At the same time, the bottom temperature is observed and the closed-loop control structure is altered if the bottom temperature falls too far on reduction of the heat carrier medium via the feed stream.

BACKGROUND

In many production processes separation problems occur, wherein a substance mixture of two or more components is to be separated into its constituents. If permitted by thermal stability, volatility and differences in boiling point of the individual substances to be separated, such separation problems in industrial production are usually solved by continuous distillation. In the simplest case of a substance mixture S consisting essentially of two components A and B, with B being higher-boiling than A under the operating conditions chosen for the distillation column used, the problem that arises is thus that of transferring B into the column bottom and A into the column top in such a way that each component is very substantially free of the respective other component. The present invention is concerned with such a separation problem—separation of a substance mixture S consisting of essentially (aside from impurities) two individual components A and B. Distillation columns suitable for such a separation problem (and also for more demanding separation problems) are fundamentally known in the prior art. The present invention is concerned with a particular closed-loop control concept for such a distillation column.

US patent specification U.S. Pat. No. 4,166,770, by contrast, is concerned with closed-loop control of a distillation column in which a feed composed of a multitude of different hydrocarbons is separated into a low-boiling top fraction and a high-boiling bottom fraction, the intention being to send the top fraction to a physical further utilization and the bottom fraction to a use as fuel. Hydrocarbon mixtures as used here as feed are regularly complex mixtures of numerous different individual components, with "a fluid transition" of the boiling points of the individual components. As a result, such mixtures have wide boiling ranges formed by the many different boiling points of the individual components. In relation to the separation of such mixtures in a distillation column, this results in the peculiarity that the temperature sensitivity of the distillation column is comparatively low in the event of changes in the reflux, for example, and has an essentially linear profile. This means that changes in temperature in the distillation column depend to a minor degree at most on the point in the distillation column at which the temperature is measured. The closed-loop control concept described in U.S. Pat. No. 4,166,770 is matched to these special boundary conditions:

The closed-loop control concept described envisages keeping the ratio of bottom stream withdrawn from the distillation column to feed stream supplied thereto very substantially constant, controlling the quality of the top stream withdrawn, in such a way that the content of (comparatively) high-boiling compounds therein must not be too great, and achieving these two aims in such a way that the distillation column can be operated with maximum energy efficiency. For this purpose, a multitude of process parameters is measured and entered into a computer, which uses these and predetermined target values to calculate signals that are transmitted to control elements (especially valves) for the reflux rate, bottoms withdrawal rate and the like. The computer is used especially in order to control the amount of fuel supplied to the evaporator of the distillation column (the evaporator is operated by the combustion of fuel oil) and the absolute reflux rate (to be distinguished from the reflux ratio) at the top of the distillation column. These two parameters in turn affect the bottoms discharge rate and the composition of the top product. Taking account of the aims mentioned—very substantially constant ratio of bottom stream withdrawn from the distillation column to feed stream supplied thereto, and quality control of the top product—the values for the amount of fuel oil to be supplied and reflux should be kept at a minimum in order to be able to operate the distillation column with maximum energy efficiency.

For this purpose, firstly, the manipulated variable of the valve for the supply of the fuel oil is determined from the difference between the target value for the mass flow rate of fuel oil and the measured actual value thereof, where the target value for the mass flow rate of fuel oil is ascertained by the computer while taking account of the feed mass flow rate, the mass flow rate of the bottom product withdrawn and the temperature of the feed, the temperature of the top product after condensation thereof (which, under the particular conditions of the separation problem described, is a measure of the composition of the top product), and the temperature of the fraction of the bottom product fed to the evaporator of the distillation column.

For this purpose, secondly, the manipulated variable of the reflux valve is determined from the difference between the target value for the reflux and the measured actual value thereof, where the target value for the reflux is ascertained by the computer while taking account of the feed mass flow rate, the mass flow rate of the bottom product withdrawn and the temperature of the top product withdrawn in gaseous form and the temperature of the top product after condensation thereof (which, under the particular conditions of the separation problem described, is a measure of the composition of the top product).

The closed-loop control concept described here is not applicable to a separation problem as described at the outset—separation of a substance mixture S composed of essentially one substance A and one substance B having significantly different boiling points—because the temperature profile of the distillation column here, as a result of the lack of a "fluid transition" of the boiling points of the individual components, does not have an essentially linear profile, and also, moreover, the distillate temperature does not permit any particular conclusions as to the composition thereof (at least not in the same way as in the case of distillation of a hydrocarbon mixture).

US patent specification U.S. Pat. No. 3,905,873 relates to a process and an apparatus for controlling a process having three variable and linked conditions, especially for control of a fractionation tower. The control unit described comprises four control systems: (1) a divider system, (2) a reflux controller system, (3) a pressure controller system and (4) a preventive system. The divider system's prime function is to control the split between distillate and bottoms. As feed flow rate increases or decreases, this divider system ensures that the distillate and bottoms flow rates accurately increase or decrease proportionately. If feed composition changes, this divider system can change the split between distillate and bottoms to ensure that product specifications are maintained. The reflux controller system regulates the reflux flow rate. As feed flow rate increases or decreases, the reflux flow rate is altered proportionately. A novel feature of this system is the use of the reflux temperature to alter the reflux flow rate if the reflux temperature deviates from a predetermined standard temperature. This system also includes means which (a) prevent the tower from becoming totally dry if feed flow is terminated, and (b) minimize the likelihood of tower flooding, i.e. filling up with liquid. The pressure controller system ensures that the tower pressure remains essentially constant. It includes a controller which regulates the heat flow rate. Heat flow is increased or decreased to maintain tower pressure constant in response to any incipient pressure changes. This system includes a manual station which permits an operator to switch between automatic and manual control. During manual control, an automatic circuit provides simple switching back to automatic control. If tower pressure is incorrect on switching back to automatic control, the heat flow will be gradually, rather than abruptly, restored to the proper rate to correct tower pressure. The preventive system ensures that the material balance of the tower is maintained. This is achieved by continually monitoring the liquid level in the tower bottom. According to the invention, the liquid level is permitted to fluctuate within predetermined limits (positions 490 and 492 in the figures) without any corrective action taking place provided the level limits are not in danger of being exceeded as determined by the relationship between a control signal which is a function of feed flow rate, feed composition, or both, and a liquid level signal.

BRIEF DESCRIPTION OF THE DRAWINGS

Various features and characteristics of the inventions described in this specification may be better understood by reference to the accompanying figures, in which.

DETAILED DESCRIPTION

Figure 1:
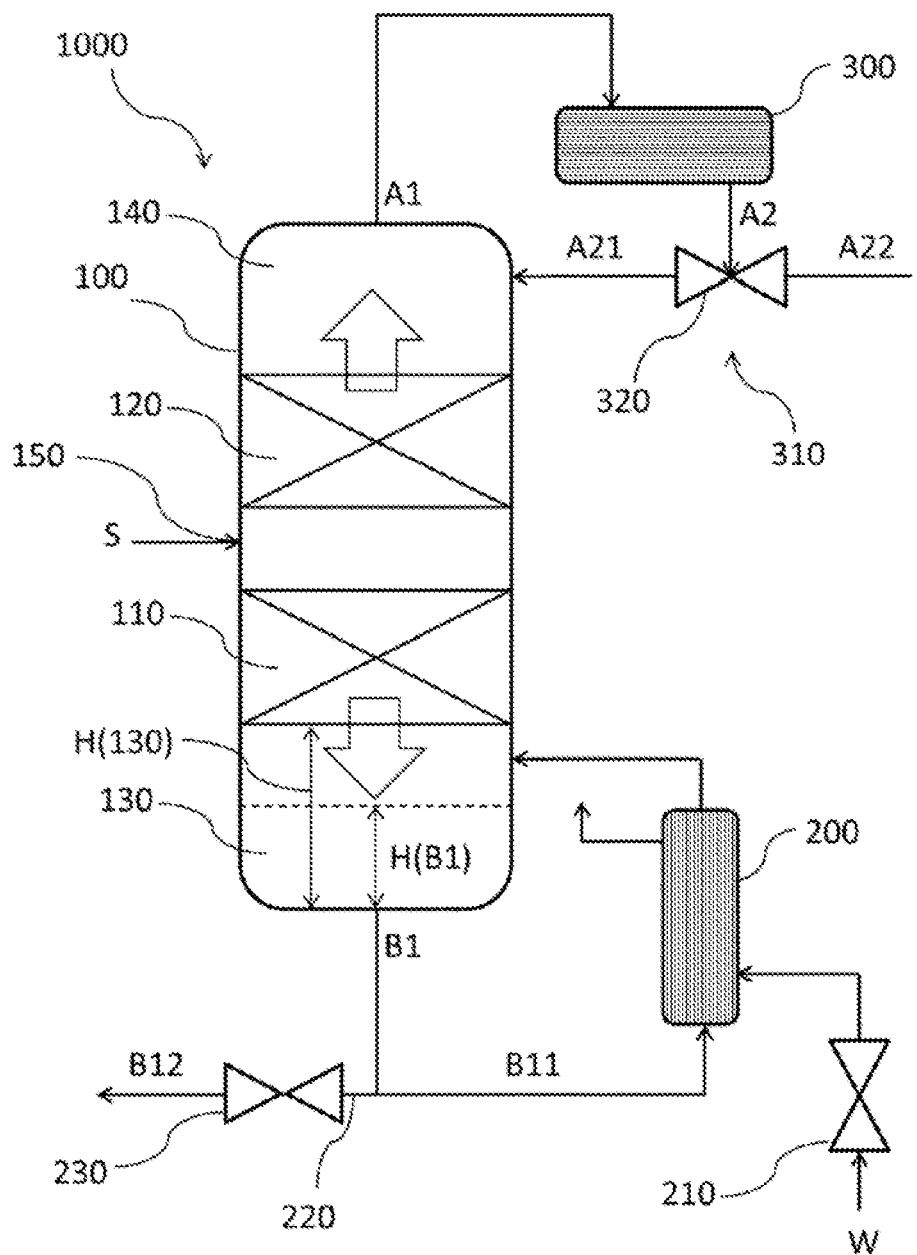
FIG. 1 shows a schematic diagram of a distillation column (1000), the operation of which can be controlled by the process of the invention.

From an economic point of view, it is of great importance to operate a distillation column in a very energy-saving manner and to keep the quality of the products of the distillation very constant and at a high level. A further aim is to configure the operation of a distillation column in a very user-friendly manner, i.e. in such a manner as to necessitate manual intervention by operating personnel only very rarely and in that case if at all possible without needing to conduct complex operations, especially also in conditions that deviate from regular operation, for instance in the event of an abrupt change in the feed mass flow rate into the distillation column.

Achievement of these aims requires efficient closed-loop control of the distillation column used for the separation problem.

The invention accordingly provides the following:

A method of continuously operating a distillation column (1000) set up for separation of a substance mixture S comprising a substance A and a substance B which is higher-boiling than substance A (under the pressure conditions chosen for the operation of the distillation column), wherein the distillation column has the following:

(I) a column body (100) in a vertical arrangement, comprising a stripping section (110) and a rectifying section (120) above it, where (at least) the stripping section has a temperature measurement device for measuring the stripping section temperature T(AT);

(II) a column bottom (130) beneath the stripping section for accommodating a liquid bottom product B1 at a bottom temperature T(B1) up to a bottoms level H(B1);

(III) a column top (140) above the rectifying section for accommodating an evaporated top product A1;

(IV) a feeding point (150) for the substance mixture S, by means of which the substance mixture S is fed to the distillation column with a flow rate ṁ(S);

(V) a circulation evaporator (200) for the heating of the column bottom by indirect heating of a first portion B11 of the liquid bottom product B1, wherein the circulation evaporator is supplied with a heat carrier medium W with a mass flow rate ṁ(W) and the circulation evaporator has a heat carrier medium valve (210) for adjustment of the mass flow rate ṁ(W);

(VI) a withdrawal unit (220) for removing a second portion B12 of the liquid bottom product B1 with a mass flow rate ṁ(B12), where the withdrawal unit has a bottoms withdrawal valve (230) for adjusting the mass flow rate ṁ(B12);

(VII) a top condenser (300) for condensing the evaporated top product A1 to obtain a liquefied stream A2;

(VIII) a recycling and withdrawal unit (310) for returning a first portion (A21) of the liquefied stream A2 to the distillation column with a mass flow rate ṁ(A21) and for removing a second portion (A22) of the liquefied stream A2 from the distillation column with a mass flow rate ṁ(A22), where the recycling and withdrawal unit has a reflux valve (320) for establishing a reflux ratio r=ṁ(A21)/ṁ(A22);

and (IX) a closed-loop control unit comprising a reflux controller (410), a bottoms level controller (420), a stripping section temperature controller (430), a bottom temperature limiting controller (440), a mass flow controller (450) for the heat carrier medium W and preferably a flow measurement device (460) for the substance mixture S supplied to the distillation column; where:

(i) for the reflux ratio r, a target value $r_{TARGET}$ within a range from r1 to r2 is defined and the reflux controller (410) uses the defined value $r_{TARGET}$ and the value for the mass flow rate ṁ(S) (preferably ascertained with a flow measurement device (460)), taking account of the minimum permissible value r1 for r, to calculate the setting of the reflux valve (320);

(ii) for the bottoms level H(B1), a target value H(B1)$_{TARGET}$ within the range from H(B1)1 to H(B1)2 is defined and the bottoms level controller (420) uses this target value H(B1)$_{TARGET}$, the current value for the bottoms level at a given time, H(B1)$_{CURR}$, and the value for the mass flow rate ṁ(S) to calculate the setting of the bottoms withdrawal valve (230);

(iii) for the stripping section temperature T(AT), a target value T(AT)$_{TARGET}$ within the range from T(AT)1 to T(AT)2 is defined and the stripping section temperature controller (430) uses this target value T(AT)$_{TARGET}$, the current value for stripping section temperature at a given time, T(AT)$_{CURR}$, and the mass flow rate ṁ(S) to calculate the setting of the heat carrier medium valve (210) and transmits the setting of the heat carrier medium valve (210) thus calculated thereto by means of the mass flow controller (450); and (iv) for the bottom temperature T(B1), a target value T(B1)$_{TARGET}$ within the range from T(B1)1 to T(B1)2 is defined and the bottom temperature limiting controller (440) is set up such that when the temperature goes below the temperature T(B1)1, the setting of the heat carrier medium valve (210), with disablement of the setting of the heat carrier medium valve (210) according to (iii), is altered such that the mass flow rate ṁ(W) is increased, and the setting of the heat carrier medium valve (210) according to (iii) is re-enabled as soon as the bottom temperature T(B1) is again within the range from T(B1)1 to T(B1)2.

This is because it has been found that, surprisingly, the aims mentioned can be achieved or are at least approached when the reflux ratio is varied as a function of the feed stream (step (i)) and, at the same time, the energy input by the heat carrier medium is altered proactively (what is called feedforward control) by accounting for the feed stream by means of feedforward control (steps (ii) and (iii)), which leads to more efficient operation of the column. This necessitates a simultaneous observation of the bottom temperature and a change in the closed-loop control structure if the bottom temperature falls too far on reduction of the heat carrier medium as a result of changes in the feed stream (feedforward control) (step (iv)).

These steps (i) to (iv), in their totality, constitute a complex multi-variable closed-loop control system or a multivariate system, where steps (i) to (iv) especially interact synergistically in the following manner:

a) Steps (i) and (iii) determine the internal column flows and ensure the balancing and matching thereof to one another, such that the required quality of the distillation can be achieved. The high thermal sensitivity of the distillation column compared to other separation problems (for example the separation of hydrocarbon mixtures discussed at the outset) is taken into account by the measurement of the stripping section temperature.

b) Step (iv) ensures that the distillation column can be operated in a robust manner and around the fixed operating range within its design (especially with regard to the temperature window in which the distillation column is to be operated, fixed operating range). The closed-loop control operation of step (iv) intervenes in the event of significant departure from the operating or design range, and hence the reliable operation of the column can no longer be assured. As soon as the operating range is attained again (as soon as the bottom temperature T(B1) is back within the range from T(B1)1 to T(B1)2), operation in the mode described under point a is resumed.

c) Steps (ii) and (iii) control the ratio of external and internal mass flow rates. The two closed loops are especially matched to one another, and the closed-loop control parameters are designed together and in combination with one another.

d) Taking account of point c, step (i) is thus also determined thereby, and the internal mass flow rates are brought into equilibrium both in the rectifying section and in the stripping section, and the desired quality of the distillation is established.

According to the invention, the distillation column (1000) is set up to separate a substance mixture S comprising a substance A and a substance B which is higher-boiling than substance A (under the pressure conditions chosen for the operation of the distillation column). This of course includes the need for the differences in boiling point between A and B to be sufficiently large to enable the removal of one substance (namely A) at the top and the removal of the other substance (namely B) in the bottom of the distillation column. This is the case especially when there is a difference in boiling point between A and B at 1.01 bar of 10° C. or more, more preferably of 25° C. or more, most preferably of 50° C. or more. In general, the difference in boiling point between A and B will not exceed 250° C.

Since substance A has a lower boiling point than substance B under the pressure conditions chosen for the operation of the distillation column, substance A is also referred to hereinafter as low boiler. It is conceivable, and does not leave the scope of the present invention, for the substance mixture S, as well as the low boiler A, also to include further compounds A' that are lower-boiling than substance B (i.e. further low boilers), especially low-boiling impurities. These are removed together with substance A at the top of the distillation column, i.e. are part of the top product A1. In an analogous manner, substance mixture S may also contain comparatively high-boiling impurities B' that accumulate in the bottom of the distillation column and become part of the bottom product B1. However, the total proportion by mass of substance A and substance B in substance mixture S is at least 90%, preferably at least 95%, more preferably at least 98%, based on the total mass of substance mixture S.

The term stripping section (AT), in the terminology of the present invention, is understood to mean the region below the feeding point (150) for the substance mixture S to be separated that includes the totality of all separating internals present in this region (for example trays or one or more structured packings) (cf. also FIG. 1 and FIG. 2, 110 therein). The stripping section temperature T(AT) is measured in the stripping section as thus understood. The position of best suitability for this temperature measurement point can be determined by the person skilled in the art, if required, in simple preliminary tests for optimization of the closed-loop control. Separating internals used are preferably structured packings, preferably 1 to 3 structured packings, especially 1 (exactly one) structured packing. In this connection, it is preferable to measure the stripping section temperature T(AT) in the middle of the structured packing (determined relative to the longitudinal direction of the distillation column) or in a region of up to 20% of the height of the structured packing above or below it (determined relative to the longitudinal direction of the distillation column). In the case of multiple structured packings arranged one on top of another, this applies to the lowermost structured packing.

Figure 2:
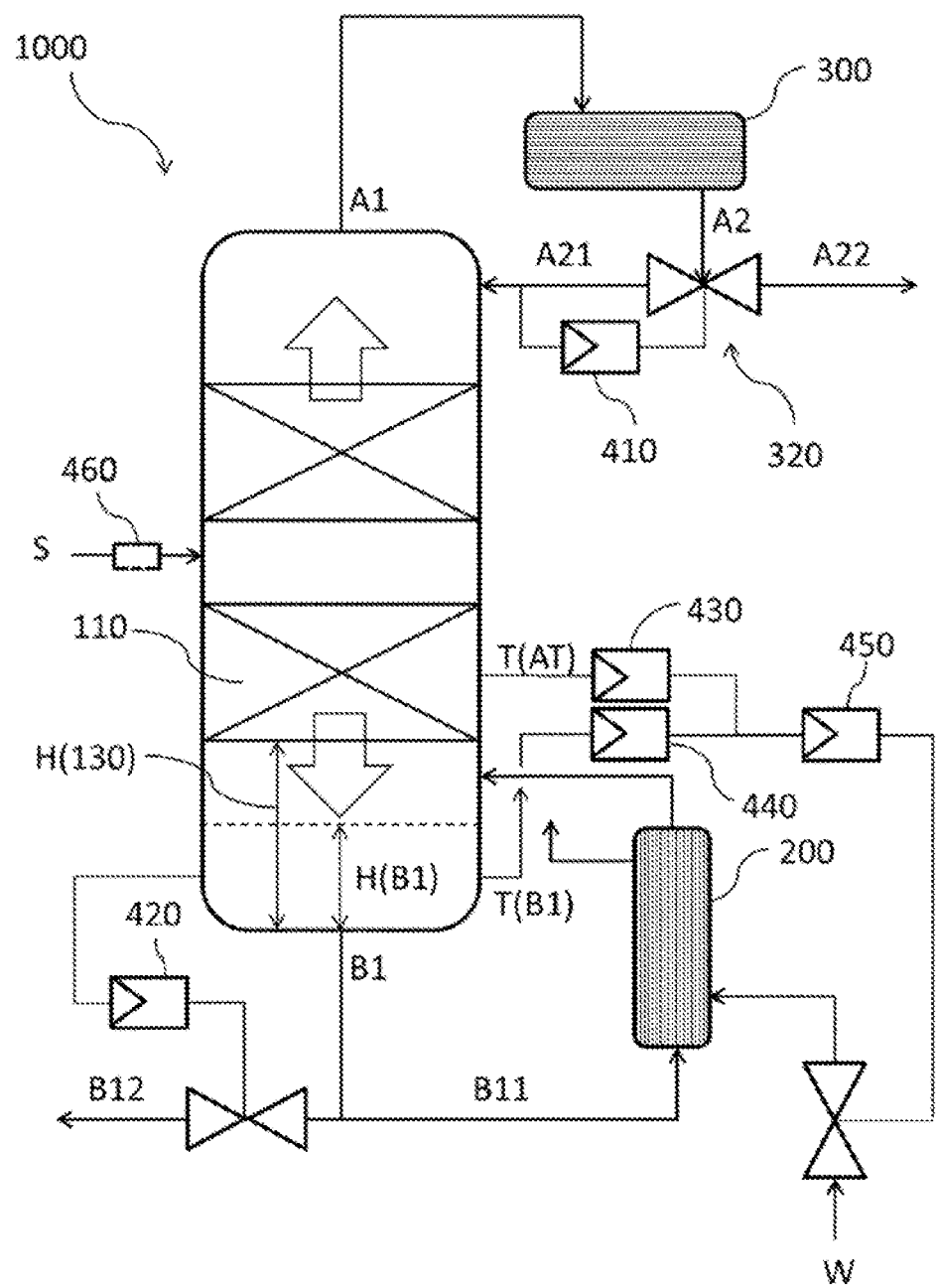
FIG. 2 shows the distillation column from FIG. 1, with inclusion of process control devices according to the invention.

The term rectifying section (VT), in the terminology of the present invention, is understood to mean the region above the feeding point (150) that includes the totality of all separating internals present in this region (cf. also FIG. 1 and FIG. 2, 120 therein). Here too, preference is given to structured packings, more preferably 1 to 3 structured packings, especially 1 (exactly one) structured packing.

The construction of such separating internals (no matter whether in the stripping or rectifying section) is known to the person skilled in the art and therefore does not require any further elucidations at this point.

The bottoms level H(B1), in the terminology of the present invention, refers to the height of the liquid level of the liquid bottom product B1 measured from the lower boundary of the distillation column (see also FIGS. 1 and 2). The expression "lower boundary of the distillation column", here and in the overall terminology of the present invention, refers to the lowest point in the internal volume of the distillation column that comes into contact with liquid bottom product in operation. The process according to the invention controls the bottoms level to the defined target value $H(B1)_{TARGET}$. This target value is within the limits $H(B1)1$ to $H(B1)2$. The actual value $H(B1)_{CURR}$, in the event of deviations from the target value $H(B1)_{TARGET}$, is thus readjusted thereto and does not fluctuate freely between $H(B1)1$ and $H(B1)2$, as is the case in the closed-loop control system according to patent specification U.S. Pat. No. 3,905,873 discussed further up (between positions 490 and 492 in that case). By contrast with the closed-loop control system described therein, the bottoms level in the process of the invention is thus kept constant (i.e., in the event of deviations from the target value $H(B1)_{TARGET}$, is readjusted thereto).

The target values to be fixed within the scope of the present invention (for the reflux ratio, the bottoms level, the stripping section temperature and the bottom temperature) are of course dependent on the nature of the separation problem and the distillation column available for the purpose. The same applies to the specific values to be calculated from the target values (for example the setting of the bottoms withdrawal valve (220)). Therefore, these values cannot be generalized and should be ascertained by the person skilled in the art for the given boundary conditions in each case, but this is a mere routine task. Typical values for the preferred employment of the separation of benzene as substance A and nitrobenzene as substance B are disclosed further down in the description and in the examples.

Figure 3:
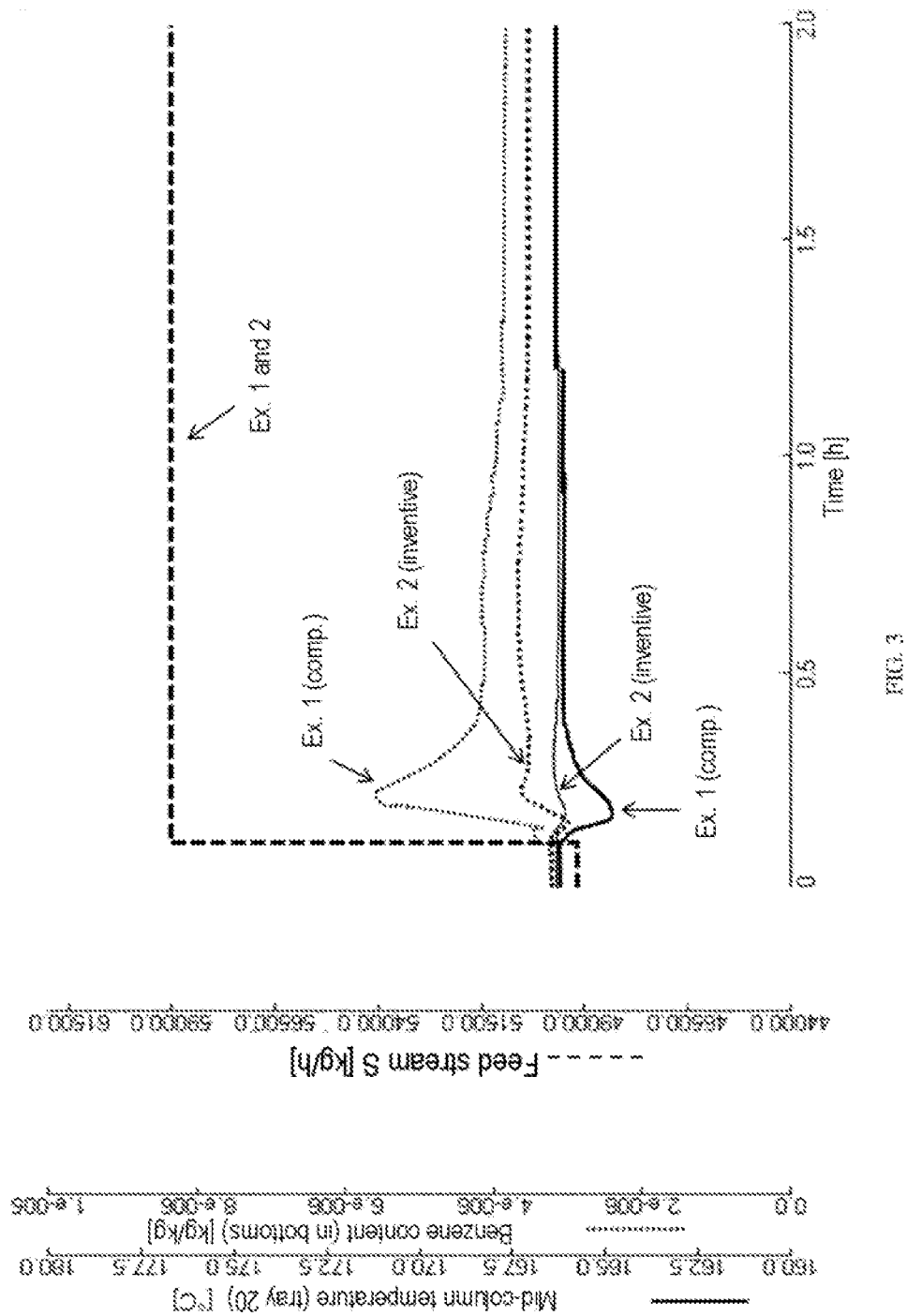
FIG. 3 shows the benzene content in the bottom product from a distillation column for separation of benzene from nitrobenzene, and the mid-column temperature in the event of a change in the feed mass flow rate of crude nitrobenzene by 20% with employment of the closed-loop control system of the invention (example 2) and without (example 1) the closed-loop control system of the invention.

The appended drawings show:

FIG. 1 a schematic diagram of a distillation column (1000), the operation of which can be controlled by the process of the invention;

FIG. 2 the distillation column from FIG. 1, with inclusion of process control devices according to the invention;

FIG. 3 the benzene content in the bottom product from a distillation column for separation of benzene from nitrobenzene, and the mid-column temperature in the event of a change in the feed mass flow rate of crude nitrobenzene by 20% with employment of the closed-loop control system of the invention (example 2) and without (example 1) the closed-loop control system of the invention.

There firstly follows a brief summary of various possible embodiments:

In a first embodiment of the process of the invention, which can be combined with all other embodiments, the closed-loop control unit comprises a flow measurement device (460) for the substance mixture S supplied to the distillation column, with which the mass flow rate ṁ(S) is ascertained in step (i).

In a second embodiment of the process of the invention, which can be combined with all other embodiments, the heat carrier medium is steam.

In a third embodiment of the process of the invention, which can be combined with all other embodiments, the substance mixture S comprises benzene as substance A and nitrobenzene as substance B.

In a fourth embodiment of the process according to the invention, which is a particular configuration of the third embodiment:

r1=55; r2=65, $H(B1)1=0.18\times H(130)$; $H(B1)2=0.42\times H(130)$, where $H(130)$ denotes the height of the column bottom measured from the lower boundary of the distillation column to the lower end of the stripping section, $T(AT)1=166°$ C.; $T(AT)2=172°$ C. and $T(B1)1=168°$ C.; $T(B1)2=173°$ C.

The embodiments outlined briefly above and further possible configurations of the invention are elucidated in detail hereinafter. The embodiments may be combined with one another as desired, unless the opposite is apparent from the context.

The appended FIG. 1 shows an example of a distillation column (1000), the operation of which can advantageously be controlled by the process of the invention. The substance mixture S to be separated is fed in laterally between rectifying section (120) and stripping section (110). The distillation column may of course also have further auxiliary units and peripheral devices known to the person skilled in the art (for example liquid collector, liquid distributor, pumps and the like). The gaseous top product A1 is condensed in top condenser (300), with guiding of a portion of the condensate (A21) as reflux back into the distillation column and withdrawal of another portion (A22) from the distillation column as top product. The mass flow ratio of reflux to withdrawal, ṁ(A21)/ṁ(A22), is referred to as reflux ratio r. The setting of the reflux ratio is undertaken with a reflux valve (320). In a departure from FIG. 1, the top condenser may also be integrated into the column body (100).

The liquid bottom product B1 fills the column bottom up to height H(B1), indicated by the dashed line. The distillation column (1000) is heated by means of a circulation evaporator (200) in which a first portion of the column bottoms discharged (namely B11) is heated indirectly with a heat carrier medium (W) and returned to the column bottom (130). Suitable heat carrier media are steam, condensate, and further liquid and gaseous heat carriers. The mass flow rate of the heat carrier medium ṁ(W) is adjusted by means of the heat carrier medium valve (210). A second portion of the column bottoms (namely B12) is discharged as bottom product, with establishment of the mass flow rate of the proportion discharged via the bottom withdrawal valve (230).

FIG. 2 shows the process control devices to be used in the context of the present invention. To simplify the drawing, some reference numerals from FIG. 1 are omitted here. The substance mixture S to be separated is first detected by means of a mass flow measuring device (460). This mass flow is utilized in order to calculate the target value for the reflux controller (410) via a defined reflux ratio (in the range of r1 to r2). The target value for the reflux ratio $r_{TARGET}$ is fixed, especially in the case of a design of the distillation column such that a very good separation can be achieved with minimal energy input. In order to assure reliable operation of the distillation column, it should be ensured that a minimum reflux ($\dot{m}(A21)_{MIN}$) is always assured. This ensures that the distillation column never runs dry. The minimum reflux ($\dot{m}(A21)_{MIN}$) is defined by choice of suitable design parameters in the design of the distillation column.

The level in the bottom of the column is controlled via the level controller (420), likewise as a function of the feed stream; this is accomplished by disturbance variable feedforward of the feed stream S.

The temperature of the stripping section T(AT) that determines the quality of the bottom product is ensured by means of a temperature controller (430). This controller uses the defined target value and the feed stream S to calculate the target value for the mass flow controller (450) for the heat carrier medium. Since it can happen in the case of significant changes in the feed stream that the bottom temperature falls below the necessary minimum temperature as a result of too small an amount of the heat carrier medium, the necessary minimum temperature is ensured by means of closed-loop temperature control (440) in the bottom of the column. This temperature controller intervenes when the temperature goes below the minimum temperature, deactivates the closed-loop control according to (iii) and reactivates it as soon as the bottom temperature is within the range of T(B1)1 to T(B1)2 again.

The heat carrier medium W used is preferably steam. However, it is likewise possible to use other heat carrier media, for example heat carrier oils.

The process of the invention is suitable for the operation of those distillation columns in which a low boiler A has to be separated from a higher-boiling product B.

An example is the separation of benzene and nitrobenzene, which is required in the context of a process for preparing nitrobenzene by nitration of benzene with nitric acid in the presence of sulfuric acid. Benzene here, especially in the adiabatically operated nitration processes that are customary nowadays, is typically used in stoichiometric excess over nitric acid, such that it has to be removed in the course of workup of the nitration product. The workup of the nitration product is typically accomplished by separating the reaction mixture present after nitration (nitration product), comprising nitrobenzene, unconverted benzene and sulfuric acid, into an aqueous sulfuric acid phase and an organic nitrobenzene phase in a first step, followed by a second step of a single-stage or multistage wash of the nitrobenzene phase, followed by a third step in which the excess benzene is separated from the washed nitrobenzene phase.

The excess benzene is typically recycled into the nitration, which results in accumulation of impurities present in the benzene originally used that pass through the nitration process essentially unchanged (such as aliphatic organic compounds in particular). Since these impurities are lower-boiling than nitrobenzene, they are distilled off together with the benzene. Excessive accumulation of these impurities is prevented by the discharge of purge streams and/or by breakdown of the impurities after a while.

This distillation problem for provision of purified nitrobenzene is advantageously implementable by the process of the invention. For this specific separation problem, preference is given to target values within the following ranges:

Reflux ratio: r1 to r2 corresponds to 55 to 65;
Bottoms level: H(B1)1 to H(B1)2 corresponds to 18% to 42% of the column bottoms level H(130) measured from the lower boundary of the distillation column to the lower end of the stripping section—see also FIGS. 1 and 2;
Stripping section temperature: T(AT)1 to T(AT)2 corresponds to 166° C. to 172° C.;
Bottom temperature: T(B1)1 to T(B1)2 corresponds to 168° C. to 173° C.

EXAMPLES

The results of the examples that follow were achieved with a distillation column for separation of excess benzene from nitrobenzene. The basic construction of the distillation column corresponded to FIG. 1.

The feed stream S consisted of crude nitrobenzene that had merely been separated from the nitrating acid and washed.

A stream of benzene and other lower-boiling compounds than nitrobenzene (especially aliphatic organic compounds) was removed overhead as stream A1.

A stream of nitrobenzene largely freed of low boilers was obtained in the bottom as stream B1.

In both examples, the feed mass flow rate S was increased by 20% during the continuous operation of the distillation column.

Example 1 (Comparative)

The feed rate of the heat carrier W (steam) was controlled as a function of the mid-column temperature (tray 20). When this temperature dropped, the feed rate of steam was increased. FIG. 3 shows, on the ordinate axis, the feed stream S (thick dashed line, in kg/h), the mid-column temperature T (at tray 20, thick solid line, in ° C.) and the concentration of benzene (the benzene content c(Bz) expressed as a proportion by mass) in the column bottom (thin dotted line, in kg benzene/kg column bottoms) as a function of the time reported on the abscissa axis t (in h).

Example 2 (Inventive)

The feed rate of the heat carrier W (steam) was controlled in accordance with the invention (cf. also FIG. 2). FIG. 3 shows, in the same way as for example 1, the feed stream S (thick dashed line), the mid-column temperature T (thin solid line) and the concentration of benzene in the column bottom c(Bz) (thick dotted line). It can be seen that, by comparison with example 1, both the mid-column temperature and the benzene concentration in the bottoms are subject to distinctly smaller fluctuations.

The invention claimed is:

1. A method of continuously operating a distillation column set up for separation of a substance mixture S consisting essentially of a substance A and a substance B which is higher-boiling than substance A, wherein the distillation column comprises:
(I) a column body in a vertical arrangement, the column body comprising a stripping section and a rectifying section arranged above the stripping section;
(II) a column bottom arranged beneath the stripping section for accommodating a liquid bottom product B1 at a bottom temperature T(B1) up to a bottoms level H(B1);
(III) a column top arranged above the rectifying section for accommodating an evaporated top product A1;

(IV) a feeding point for the substance mixture S, the feeding point being configured to feed the substance mixture S to the distillation column with a flow rate $\dot{m}(S)$;

(V) a circulation evaporator configured to heat the column bottom by indirect heating of a first portion B11 of the liquid bottom product B1, wherein the circulation evaporator is supplied with a heat carrier medium W with a mass flow rate $\dot{m}(W)$ and the circulation evaporator has a heat carrier medium valve for adjustment of the mass flow rate $\dot{m}(W)$;

(VI) a withdrawal unit configured to remove a second portion B12 of the liquid bottom product B1 with a mass flow rate $\dot{m}(B12)$, where the withdrawal unit has a bottoms withdrawal valve configured to adjust the mass flow rate $\dot{m}(B12)$;

(VII) a top condenser configured to condense the evaporated top product A1 to obtain a liquefied stream A2;

(VIII) a recycling and withdrawal unit configured to return a first portion of the liquefied stream A2 to the distillation column with a mass flow rate $\dot{m}(A21)$ and for removing a second portion of the liquefied stream A2 from the distillation column with a mass flow rate $\dot{m}(A22)$, where the recycling and withdrawal unit comprises a reflux valve configured to establish a reflux ratio $r=\dot{m}(A21)/\dot{m}(A22)$; and (IX) a closed-loop control unit comprising a reflux controller, a bottoms level controller, a stripping section temperature controller, a bottom temperature limiting controller and a mass flow controller for the heat carrier medium W;

wherein the method comprises:
(i) defining, for the reflux ratio r, a target value $r_{TARGET}$ within a range from r1 to r2, wherein the reflux controller uses $r_{TARGET}$ and the value for the mass flow rate $\dot{m}(S)$, taking account of the value of r1 for r, to calculate the setting of the reflux valve;

(ii) defining, for the bottoms level H(B1), a target value $H(B1)_{TARGET}$ within the range from $H(B1)1$ to $H(B1)2$, wherein the bottoms level controller uses $H(B1)_{TARGET}$, the bottoms level at a given time, $H(B1)_{CURR}$, and the mass flow rate $\dot{m}(S)$ to calculate the setting of the bottoms withdrawal valve;

(iii) defining, for a stripping section temperature T(AT), a target value $T(AT)_{TARGET}$ within the range from $T(AT)1$ to $T(AT)2$, wherein the stripping section temperature controller uses $T(AT)_{TARGET}$, the stripping section temperature at a given time, $T(AT)_{CURR}$, and the mass flow rate $\dot{m}(S)$ to calculate the setting of the heat carrier medium valve and transmits the setting of the heat carrier medium valve thus calculated thereto by means of the mass flow controller;

(iv) defining, for the bottom temperature T(B1), a target value $T(B1)_{TARGET}$ within the range from $T(B1)1$ to $T(B1)2$, wherein the bottom temperature limiting controller is set up such that when the temperature goes below the temperature $T(B1)1$:
(1) the setting of the heat carrier medium valve according to (iii) is disabled;
(2) the setting of the heat carrier medium valve is altered such that the mass flow rate $\dot{m}(W)$ is increased; and
(3) the setting of the heat carrier medium valve according to (iii) is re-enabled as soon as the bottom temperature T(B1) is again within the range from $T(B1)1$ to $T(B1)2$.

2. The method as claimed in claim 1, in which the closed-loop control unit comprises a flow measurement device for the substance mixture S supplied to the distillation column, with which the mass flow rate $\dot{m}(S)$ is ascertained in step (i).

3. The method as claimed in claim 1, in which the heat carrier medium comprises steam.

4. The method as claimed in claim 1, in which the substance mixture S comprises benzene as substance A and nitrobenzene as substance B.

5. The method as claimed in claim 4, in which:
r1=55; r2=65,
H(B1)1=0.18×H(130); H(B1)2=0.42×H(130), where H(130) denotes the height of the column bottom measured from the lower boundary of the distillation column to the lower end of the stripping section,
T(AT)1=166° C.; T(AT)2=172° C. and
T(B1)1=168° C.; T(B1)2=173° C.

* * * * *